United States Patent
Marszalek

(10) Patent No.: US 6,847,216 B2
(45) Date of Patent: Jan. 25, 2005

(54) METHOD AND APPARATUS FOR STABILIZING PARASITIC ERROR CAPACITANCE IN OIL QUALITY SENSORS

(75) Inventor: Gary A. Marszalek, South Lyon, MI (US)

(73) Assignee: Detroit Diesel Corporation, Detroit, MI (US)

( * ) Notice: Subject to any disclaimer, the term of this patent is extended or adjusted under 35 U.S.C. 154(b) by 85 days.

(21) Appl. No.: 10/426,131

(22) Filed: Apr. 28, 2003

(65) Prior Publication Data

US 2004/0212375 A1 Oct. 28, 2004

(51) Int. Cl.⁷ .................. G01R 27/08; G01R 27/26
(52) U.S. Cl. .................. 324/698; 324/658; 324/661; 324/663
(58) Field of Search .................. 324/698, 658, 324/661, 663

(56) References Cited

U.S. PATENT DOCUMENTS

| | | | |
|---|---|---|---|
| 5,604,441 A | 2/1997 | Freese et al. | 324/663 |
| 5,611,240 A * | 3/1997 | Yamaguchi | 73/304 C |
| 6,268,737 B1 | 7/2001 | Marszalek | 324/663 |
| 6,278,282 B1 | 8/2001 | Marszalek | 324/663 |
| 6,320,393 B1 * | 11/2001 | Yasui et al. | 324/663 |

* cited by examiner

Primary Examiner—Anjan Deb
Assistant Examiner—John Teresinski
(74) Attorney, Agent, or Firm—Fildes & Outland, P.C.

(57) ABSTRACT

A sensor for detecting changes in the dielectric constant of a liquid is described. The sensor has two electrodes immersed in the liquid with dielectric surfaces substantially parallel with each other, and a ramp disposed on a support between the electrodes. The ramp intersects the surfaces at obtuse and acute angles respectively and provides a surface disposed at an angle relative to an electric field extending between the two electrodes, thereby reducing parasitic effects of the sensed dielectric content of the liquid. Slots in the electrode adjacent the lower end of the ramp reduce the strength of the field proximate to the ramp and thereby further reduce the parasitic effects.

12 Claims, 2 Drawing Sheets

METHOD AND APPARATUS FOR STABILIZING PARASITIC ERROR CAPACITANCE IN OIL QUALITY SENSORS

TECHNICAL FIELD

This invention relates to a method and apparatus for detecting the presence of contaminants in lubricating oils and more particularly to a method and dielectric sensor apparatus that accurately measures the amount of polar and/or colloidal contaminants in diesel engine lubricating oil.

BACKGROUND OF THE INVENTION

Oil quality sensors are known to sense variations in the dielectric constant of petroleum and synthetic lubricating oils. The sensed variations of the dielectric constant of engine oil are compared with a baseline reading of fresh lubricating oil to reveal the presence of contaminants such as soot dissolved in the oil, liquids, emulsified liquids, and particles. The theory behind this sensing technique is that the dielectric constant of the oil is related to the concentration of contaminants in the oil. Assuming the oil is a perfect insulator, the capacitive reactance $X_c$ of the oil can be expressed as:

$$X_c = 1/(2\pi f C),$$

where f is the frequency of a potential applied across the sensor, and C is the capacitance of the oil.

While the capacitive reactance can be measured with little error in non-polar oil, measurement error increases with increasing conductivity of the oil due to a solution current flowing through the oil.

Generally, newly refined oil stock is a non-polar solution. When it is formulated for lubricating oil, various additives are added to improve performance and extend the useful life of the oil. Many of these additives, however, are polar in nature and their polarities increase with increasing temperature. Even as "new" oil reaches operating temperatures, minor solution current can be detected. Solution current also increases as contaminants increase in the oil during use.

Prior art methods and systems utilize an unbalanced alternating current (AC) or static direct current (DC) potential that causes migration of polar contaminants toward oppositely charged sensor electrodes. This contaminant migration results in the build up of contaminants on the electrodes that shield the electrodes from further charge transfer and can contribute to the erroneous measurement of the capacitive reactance of the oil.

A prior approach used to reduce contaminant build up on the electrodes has been to coat one or both of the electrodes with a non-stick surface such as Teflon®. This approach, however, is not effective on polar contaminant migration toward the electrodes. This polar contaminant migration eventually causes liquid dielectric measurement error which can be larger in scale than the inherent or true value of the liquid dielectric measurement. Furthermore, these errors can be exacerbated in low-frequency measurements used in oil quality sensing because the error can manifest itself in an error condition referred to as a double layer capacitance (DLC) error.

Errors resulting from double layer capacitance occur because solid phase conductors only are used as electrodes wherein charges are carried along by a migration of electrons. In solution such as engine lubricating oil, charges are transferred through a migration of ions in the oil. The ions exist in a solution that is in a different phase. Where two phases meet or interface, chemical reactions occur. Such a reaction often includes contaminated molecules such as polarized molecules which disassociate, thereby forming separate positive ions and negative ions within the lubricating oil. The disassociation produces remnants known as solvation shells. Over time, these remnants or artifacts impede ion access and shield the electrodes from further charge transfer. Localized charges, therefore, accumulate around electrodes causing double layer capacitance error.

Another error causing condition associated with liquid dielectric sensing is a condition referred to as surface wetting buildup which results from contaminants accumulated on an insulator surface disposed between two electrodes with the insulator surface parallel to electrostatic lines of force generated by the two electrodes. Surface wetting buildup typically exists on fabricated insulators used to support, seal and separate measurement electrodes at the base of a sensor. In order to reduce the measurement error, frequent cleaning of the insulator surface is needed. This may not be practical in some situations because of the structural complexity of a system. Furthermore, it is desirable to keep a sensor in use with as little contaminant accumulation as possible. Generally, in moderately contaminated oil, contaminants accumulate between electrodes that cause parasitic error capacitance which results in inaccurate measurements from increased sensed capacitance.

SUMMARY OF THE INVENTION

The present invention provides a liquid dielectric sensor for detecting the presence of contaminants in lubricating oils and reducing measurement errors caused by solution current in the oil.

The present invention also provides a liquid dielectric sensor for reducing the presence of contaminants that deposit on an area interposed between the electrodes. Thereby errors in capacitance measurement are reduced.

The present invention further provides a liquid dielectric sensor that reduces electric field strength in an area between electrodes that contributes significantly toward reducing measurement errors.

In accordance with the invention, a sensor adapted to be disposed in a flow of fluid for detecting changes in the dielectric constant of the liquid includes a first elongated electrode member having a metallic core and a first dielectric, fluid contacting surface. The sensor also includes a second elongated electrode member having a metallic portion and a second dielectric, fluid contacting surface. A support supports the electrodes and the fluid contacting surfaces in a spaced, substantially parallel disposition with the first and second dielectric, fluid contacting surfaces facing one another to accommodate the circulation of fluid through the space between the electrodes. This space or gap accommodates a ramp which is disposed on the support between the dielectric surfaces of the electrodes. The ramp intersects the first and second contacting surfaces at obtuse and acute angles respectively, and provides a surface angularly disposed relative to an electric field extending between the electrodes. Thereby, the parasitic effects of the sensed dielectric constant of the liquid are reduced.

Accordingly, an oil condition sensor includes a housing having a cylindrical sidewall with an inner surface forming part of a first electrode. The housing includes at least one opening for accommodating a flow of oil therethrough. The first electrode has a metallic core and a first dielectric, fluid contacting inner surface. The oil condition sensor also includes a member concentrically disposed within the housing. The member has an outer surface forming part of a second electrode spaced from the inner surface. The second electrode has a metallic core and a second dielectric, fluid contacting outer surface. The inner and outer dielectric, fluid contacting surfaces are substantially parallel in disposition. A ramp is disposed within the space between the inner and outer surfaces at obtuse and acute angles respectively. The ramp has a surface angularly disposed relative to the electric field which couples the first and second electrodes. Thereby, the parasitic effects of the sensed dielectric constant of the liquid are reduced.

Accordingly, a method for sensing a variation in the dielectric constant of a liquid uses a first elongated electrode member that has a metallic core and a first dielectric, fluid contacting surface. The method also uses a second elongated electrode member that has a metallic portion and a second dielectric, fluid contacting surface. A support supports the electrodes and the fluid contacting surfaces in a spaced, substantially parallel disposition with the first and second dielectric, fluid contacting surfaces facing one another to accommodate the circulation of fluid through the space between the electrodes. The method includes the steps of disposing a parasitic incline between the first and second dielectric, fluid contacting surfaces, and applying alternating current to the electrodes. The method also includes the step of generating an electric field between the electrodes, causing the strength of the electric field proximate to the parasitic incline to be relatively weaker than the strength in other regions between the electrodes. Thereby, errors in the measurement of the dielectric constant of the liquid are reduced.

These and other features and advantages of the invention will be more fully understood from the following detailed description of the invention taken together with the accompanying drawings.

DESCRIPTION OF A PREFERRED EMBODIMENT

Figure 1:
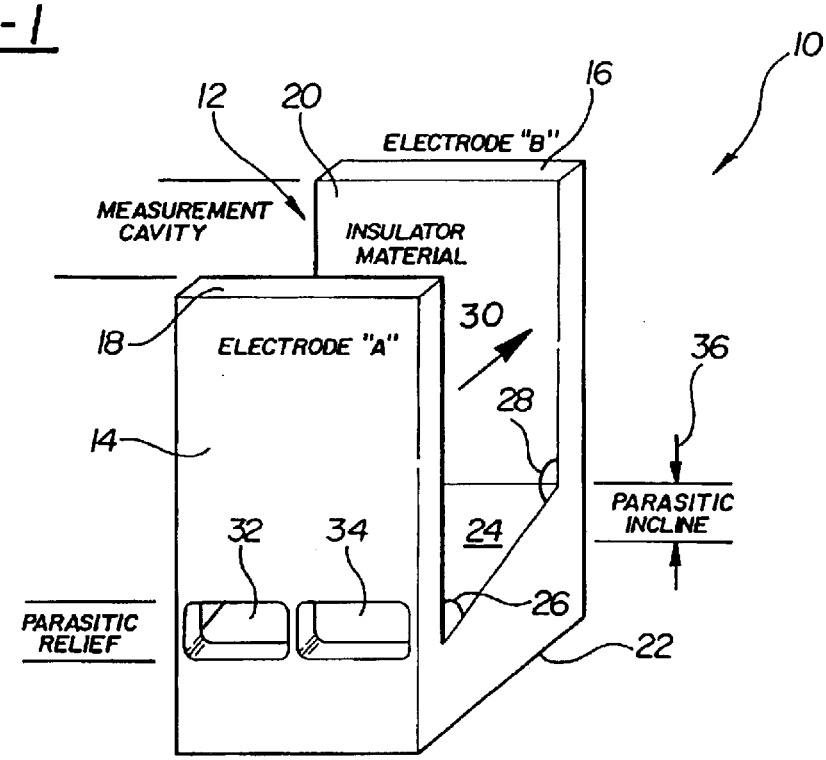
FIG. 1 is a perspective view of a basic embodiment of a liquid dielectric sensor according to the invention.

Referring now to the drawings in detail, FIG. 1 shows a sensing device 10 of a liquid dielectric sensor for determining the quality of a liquid such as lubricating oil. The liquid is caused to flow through an electric field generated in a space 12 between a first electrode 14 and a second electrode 16. The pair of electrodes 14, 16 is preferably coupled to a power source (not shown) which generates a balanced alternating current that generates an electric field between the electrodes 14, 16. Each of the electrodes 14, 16 preferably includes an elongated metallic core covered by a dielectric material having a dielectric, fluid contacting surface 18, 20 respectively, that is adapted for direct contact with the liquid. The metal cores of the electrodes 14, 16 are not in direct contact with the liquid because it is desirable to have a solid phase nonconducting material such as Teflon® in direct contact with liquid for the purpose of reducing electrical double layer capacitance measurement error.

A supporting member 22 supports the pair of electrodes 14, 16 including the fluid contacting surfaces 18, 20 in a substantially parallel disposition to permit the circulation of the liquid through the space 12 between the electrodes 14, 16. Support 22 is formed of any suitable nonconductive material. For example, support 22 can be a solid phase dielectric material such as Teflon®. Support 22 can be comprised of electrically conducting materials, but electric isolation with the electrodes 14, 16 must be maintained. Support 22 may be a jacket which forms a contiguous whole with the contacting surfaces 18, 20 constituting identical material such as Teflon®.

A ramp 24 is disposed on support 22 between the electrodes 14, 16. Ramp 24 defines a substantially flat surface that intersects the first and second contacting surfaces 18, 20 at a pair of angles, acute angle 26 and obtuse angle 28. Preferably, acute angle 26 is about 45 degrees, and obtuse angle 28 is about 135 degrees. An electric field 30 generated between the first and second electrodes 14, 16 extends normal to the surfaces 18, 20 so that ramp 24 forms an angle with the electric field 30. The non-parallel disposition of ramp 24 in relation to electric field 30 reduces parasitic effects such as parallel surface wetting.

To further reduce parasitic effects, the metal portions that contribute most to parasitic effects are removed. This is accomplished by removing metal portion of electrodes 14, 16 in the proximity of the ramp 24. Since the fluid that flows close to ramp 24 contributes the most to surface wetting on ramp 24 when electric field 30 is applied, the elimination or removal of portions of the electrode that contributes to the electric field in the proximity of ramp 24 reduces the parasitic effect of surface wetting. Thus, parasitic relief slots 32, 34 are provided to reduce electric field strength in the proximity of ramp 24.

However, other forms of removal can be applied as well. By way of an example, by just removing some metal in the same area without forming slots, the purpose can be accomplished as well because electric field strength is reduced in the area. In addition, the slots 32, 34 may be located further away from the ramp 24. It is noted that relief slots 32, 34 reduce the electric field strength by eliminating or reducing the strength of field lines adjacent to ramp 24. A parasitic effect reducing incline 36 is defined by the positioning of ramp 24 to form the acute and obtuse angles 26, 28. Parasitic incline 36 has the effect of reducing surface wetting of undesirable substances such as polarized artifacts upon ramp 24 surface.

The above structure described in FIG. 1 increases the accuracy of capacitance measurement in two respects. First, contacting surfaces 18, 20 together with ramp 24 constitute a dielectric material member of a solid phase type. Preferably, the dielectric material is formed out of Teflon® material. Thereby, a cavity is provided in the above structure. In this cavity, the interface between liquid solution and solid insulator does not involve a metal portion coming into direct contact with liquid solution. It should be noted that electrode is defined in this application to include a metal core or portion, as well as part of a solid phase insulator covering thereof. For example, Teflon® may be used as the solid insulator covering thereof. The end result is that no metal portions of electrodes 14, 16 are in direct contact with fluid. Because the electrode/solution boundary is now between insulator contacting surfaces 18, 20 and liquid, solution currents and localized charge/separation issues are reduced.

Cavity insulators such as Teflon® material are chosen based on their electrical properties, dimensional stability, temperature stability, chemical compatibility, and other fundamental dielectric parameters. The reason for the above choices is that since a dielectric material is interposed between the electrodes 14, 16, the dielectric material's physical characteristics are necessarily measured along with the physical characteristics of liquid between electrodes 14, 16. The dielectric material contributes toward the measurement by virtue of is disposition between the electrodes 14, 16.

The sensitivity of such measurement assemblies is dependent upon the ratio of measurement cavity to insulator material interposed between the metal portions of the electrodes. Insulator/cavity ratios are tailored to fit a specific performance sensitivity requirement of a particular application. This is because the liquids subject to measurement may have different physical characteristics such as different degrees of polarization.

With regard to ramp 24, a sloped insulator between the electrodes reduces the parasitic effect upon the surface between the electrodes by providing a parasitic effect reducing incline 36 which is defined by angles 26, 28, and the ramp surface 24. In addition, by removing portions of the electrodes that contributes most toward surface wetting, for example slots 32, 34, parasitic effect is further reduced. However, electrode structural integrity must also be maintained. Therefore, the removal of electrode material needs to be balanced against the structural integrity of the sensor.

Figure 2:
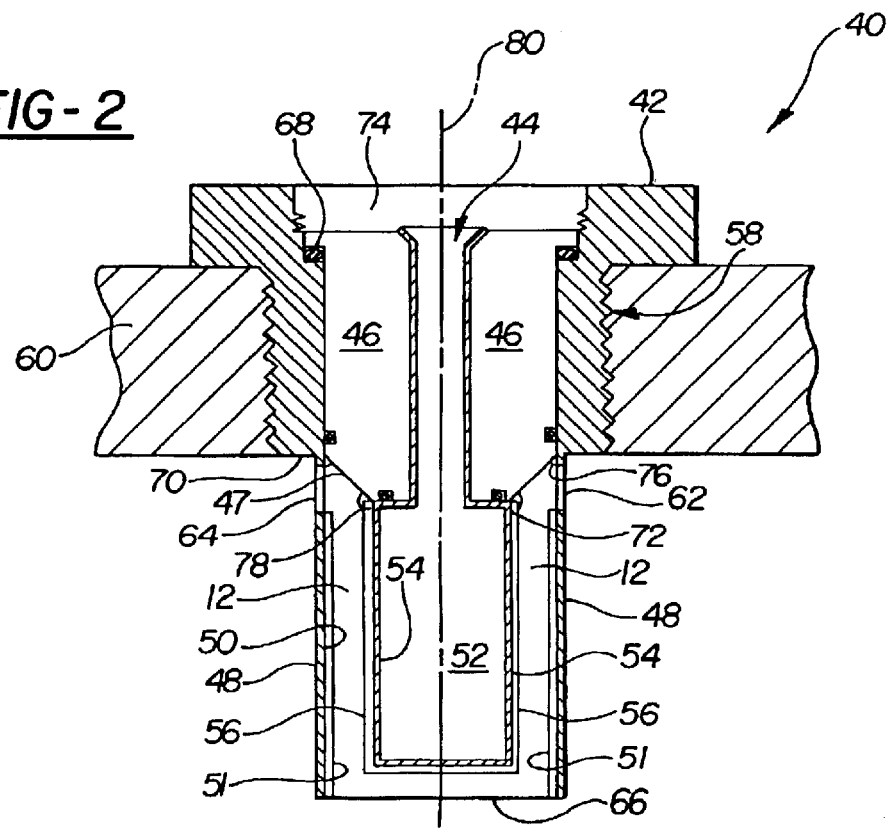
FIG. 2 is a sectional elevational view of another embodiment of a liquid dielectric sensor.

FIG. 2 is a sectional view of a preferred exemplary embodiment of a liquid dielectric sensor 40 according to the present invention. The sensor 40 includes a conductive housing member 42, a conductive inner member 44, and a non-conductive supporting member 46 that has a ramp 47 which is interfitted as shown.

The housing member 42 includes a cylindrical portion 48 with an inner surface 50, and forms a first electrode. A layer 51 of a solid phase dielectric covers inner surface 50. The inner member 44 includes a cylindrical portion 52 with an outer surface 54, and forms a second electrode. Outer surface 54 is covered by a layer 56 of a solid phase dielectric material which is contiguous with layer 51 of solid phase dielectric. The inner member 44 is secured within the housing member 42 such that the outer cylindrical portion 48 and the inner cylindrical portion 52 define an oil deterioration sensor capacitor. The first electrode is defined to include inner surface 50, and the dielectric layer 51. The second electrode is defined to include outer surface 50 and layer 56. Dielectric layers 51, 56 may be part of a whole piece of a dielectric jacket formed from a dielectric material such as Teflon® material.

The housing member 42 also includes a threaded outer surface 58 which, in a preferred embodiment, is adapted to be threaded into an oil container 60 of an internal combustion engine. The scope of the present invention additionally contemplates applications which do not involve combustion but where oil is still monitored for degradation, e.g., compressors, pumps, and gearboxes.

The housing member 42 is open ended to allow oil to enter into the cylindrical portion 48. An outer end 66 of the cylindrical portion 48 is open to allow the free flow of lubricating oil through the space 12 between the electrodes. Gaskets 68, 70 are disposed between housing member 42 and supporting member 46 for sealing therebetween in order to keep liquid between electrodes from leaking into region 74, wherein electronic components may be placed. Gasket 72 is disposed between inner member 44 and supporting member 46 for sealing therebetween. A power source generating an alternating electric field is applied to both electrodes.

It is noted that the sensor 40 may additionally include other electrodes (not shown) located in the proximity of ramp 47. Supporting member 46 is preferably a solid dielectric material such as Teflon® which can form a contiguous whole with layers 51 and 56. Alternatively, supporting member 46 may be an independent piece stacked between the two electrodes. Ramp 47 and inner surface 50 defines an acute angle 76. Similarly, ramp 47 and outer surface 50 define an obtuse angle 78. The acute angle 76 and obtuse angles 78 are preferably about 45 degrees and 135 degrees respectively.

Various parts of liquid dielectric sensor 40 form a substantially, cylindrically symmetric whole around an axis 80. The various cylindrical shapes described above include pairs of points that are symmetrical in relation to each other. Between electrodes, this symmetric disposition is important in that migrations of polar particles in liquid are reduced because the frequent changes in polarity of the electrodes now exert a symmetric effect upon sensor 40 by virtue of this geometrically symmetric structure.

It should be noted that liquid does not directly contact the metal of the electrodes. Dielectric layers 51, 56 are interposed between liquid and the metal potions of electrodes respectively.

Figure 3:
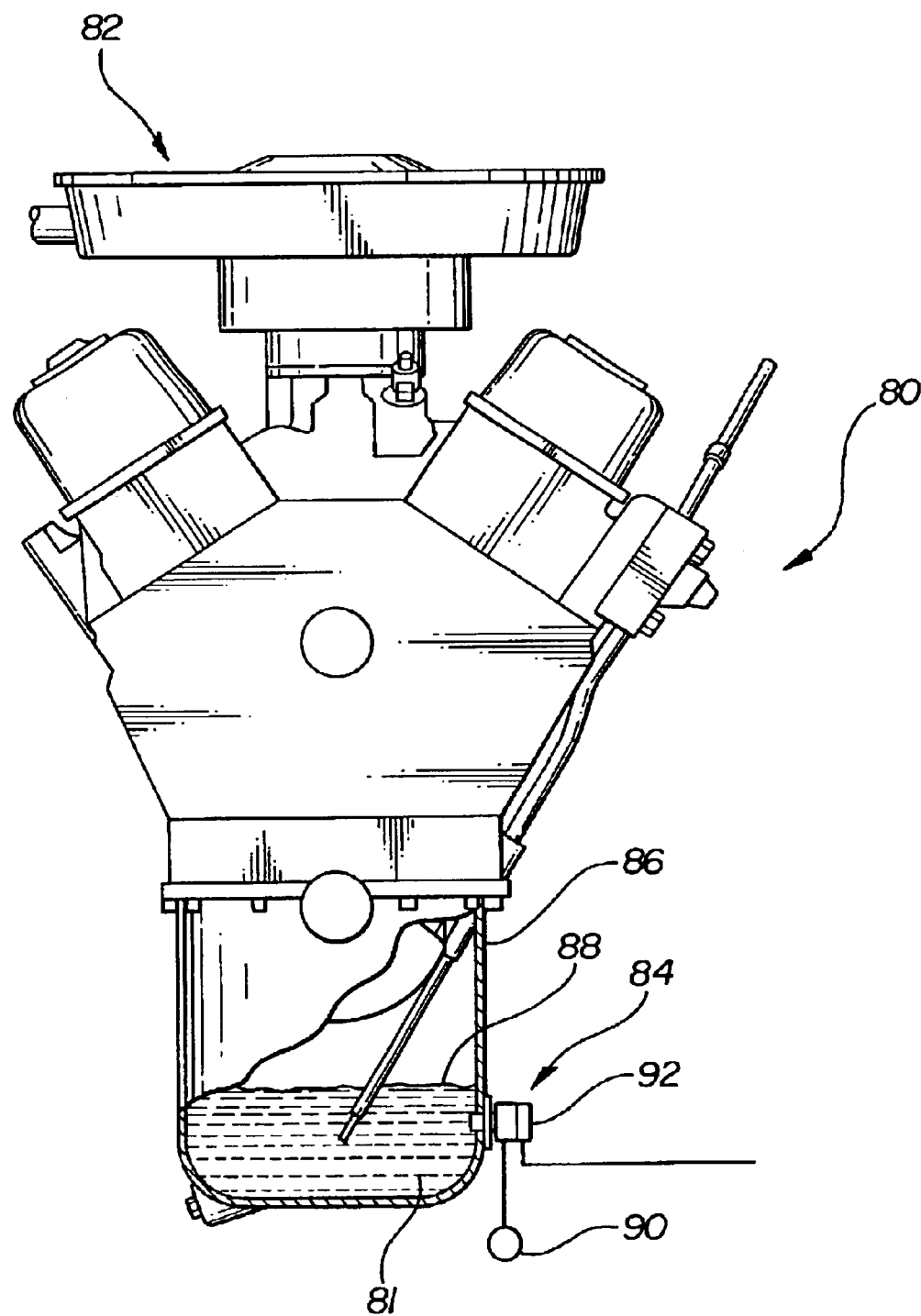
FIG. 3 is a schematic environmental diagram of an engine including a system for determining oil quality according to the invention and having an oil quality sensor mounted in an oil reservoir the engine.

Referring to FIG. 3, system 80 is provided for determining the quality of oil 81 in a motor vehicle engine 82. The system 80 includes a sensor 84 which may be the liquid dielectric sensor 40 in FIG. 2 that is adapted to be mounted on the wall 86 of an oil reservoir 88. The sensor 84 includes spaced electrodes that are adapted to be immersed in the lubricating oil. Metal portions of the electrodes are insulated to prevent their contacting lubricating oil, at least in the space between the electrodes. Lubricating oil disposed between the electrodes serves as a predominantly dielectric portion subject to measurement. However, the solid phase dielectric material disposed on the metal portions of the electrodes contributes toward the accuracy of the oil quality measurement.

As further shown in FIG. 3, the sensor 84 is connected to a power source 90 for applying a time-varying potential, such as an AC potential, across the electrodes. By way of an example, a power source 90 may include a motor vehicle battery and an AC converter. Preferably, the power source 90 cooperates with a control circuit 92 to provide a substantially symmetrically balanced sinusoidal AC potential across the electrodes so that no significant DC bias is created across the electrodes.

In order to increase capacitance measurement accuracy, the present invention provides a liquid measurement cavity or space 12 that is disposed to receive liquid 81 such as lubricating oil. This liquid measurement cavity 12 is enclosed in a dielectric material such as a Teflon® jacket. Two electrically conducting electrodes respectively are kept apart or free from direct contact with the liquid 81. The interface, or connecting surface interposed between the liquid and the solid material, does not involve any electrically conducting materials of a solid phase type. At both sides of the interfaces, there are no solid phase electrically conducting materials. The electrodes (or the metal portions thereof) are free from direct contact with the fluid.

The sensitivity of measurement is also dependent upon the size of the measurement cavity in relation to the quantity of the insulated materials. Therefore, insulator/cavity ratios can be tailored to fit a specific performance sensitivity requirement. For example, the thickness of the Teflon® jacket can vary.

A ramp such as ramps 24, 47 in FIGS. 1 and 2 respectively are introduced to reduce known effects of surface wetting in parallel insulators. Parallel insulator is defined as an insulator having a surface contacting a measured liquid 81, and having the surface disposed between electrode surfaces at substantially 90 degrees respectively. However, when a wetted parallel field insulator surface lies between measurement electrodes, error capacitance occurs because of undesirable material depositing on the surface with the deposit caused, in part, by the parallel electric field. Over time, this deposit accumulates, and error can increase significantly. Therefore, a ramp, or a sloped insulator surface, such as ramp 24 or ramp 47 in FIG. 1 or 2 respectively, reduces the error capacitance because the above surfaces are intentionally kept non-parallel with an electric field coupling two electrodes. Further, by removing portions of electrode material that contributes toward electric fields that are parallel with ramp 24 or ramp 47, measurement error is reduced.

Furthermore with continued reference to FIG. 2, through the removal of electrode material from around the vicinity encompassing the inclined or sloped insulator, the portions of the electrical field in proximity with the slope are reduced. This can be accomplished by providing slots 62, 64 in the cylindrical portion 48. However, electrode structural integrity must also be maintained. Therefore, a balance needs to be kept in that removing some electrode material around the inclined insulator needs to be balanced against the structural integrity of the electrode and surrounding materials. In addition, the ramp also helps with regard to parallel fields symptoms caused by portions of electrode material that must structurally remain in the proximity of the ramp. For example, some material that is between the slots 62, 64 needs to remain for the sensor's structural integrity. The slots 62, 64 are preferably located next to the bottom or lower end of the ramp and have a height about equal to the height 36 at the top or upper end of the ramp. The result is that the electric field that extends normal to the opposed surfaces of the electrodes is reduced over the total length of the ramp surface.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A sensor adapted to be disposed in a flow of fluid for detecting changes in the dielectric constant of the liquid, the sensor comprising:
    a first elongated electrode member having a metallic core and a first dielectric, fluid contacting surface;
    a second elongated electrode member having a metallic portion and a second dielectric, fluid contacting surface;
    a support supporting the electrodes and the fluid contacting surfaces in a spaced, substantially parallel disposition with the first and second dielectric, fluid contacting surfaces facing one another to accommodate the circulation of fluid through the space between the electrodes; and
    a ramp disposed on the support between the dielectric surfaces of the electrodes;
    the ramp intersecting the first and second contacting surfaces at obtuse and acute angles respectively and providing a surface angularly disposed relative to electric field coupling between the first and second electrode, thereby reducing parasitic effects of the sensed dielectric constant of the liquid.

2. The sensor of claim 1, wherein the acute and obtuse angles are about 45 degrees and 135 degrees respectively.

3. The sensor of claim 1 including at least one port disposed proximate to the ramp and allowing liquid flow therethrough.

4. The sensor of claim 3, wherein the port is disposed along a bottom of the ramp.

5. An oil condition sensor, comprising:
    a housing having a cylindrical side wall with an inner surface defining a first electrode, the housing including at least one opening for accommodating a flow of oil therethrough, the first electrode having a metallic core and a first dielectric, fluid contacting inner surface;
    a member concentrically disposed within the housing and having an outer surface defining a second electrode spaced from the inner surface, the second electrode having a metallic core and a second dielectric, fluid contacting outer surface;
    the inner and outer dielectric, fluid contacting surfaces being substantially parallel in disposition;
    a ramp disposed within the space between the inner and outer surfaces at obtuse and acute angles respectively, the ramp having a surface angularly disposed relative to electric field coupling between the first and second electrodes, thereby reducing parasitic effects of the sensed dielectric constant of the liquid.

6. The sensor of claim 5, wherein the acute and obtuse angles are about 45 degrees and 135 degrees respectively.

7. The sensor of claim 5 including at least one port disposed proximate to the ramp and allowing liquid flow therethrough.

8. The sensor of claim 7, wherein the port is disposed along a bottom of the ramp.

9. A method for sensing a variation in the dielectric constant of a liquid using a first elongated electrode member having a metallic core and a first dielectric, fluid contacting surface; a second elongated electrode member having a metallic portion and a second dielectric, fluid contacting surface; a support supporting the electrodes and the fluid contacting surfaces in a spaced, substantially parallel disposition with the first and second dielectric, fluid contacting surfaces facing one another to accommodate the circulation of fluid through the space between the electrodes; said method comprising the steps of:
    disposing a parasitic incline between the first and second dielectric, fluid contacting surfaces;
    applying alternating current to the electrodes; and
    generating an electric field between the electrodes, causing the strength of the electric field proximate to the parasitic incline to be relatively weaker than the strength in other regions between the electrodes, thereby reducing errors in the measurement of the dielectric constant of the liquid.

10. The method of claim 9 including the step of computing the dielectric constant.

11. The method of claim 9 including the step of reading an output.

12. The method of claim 9, wherein the parasitic incline is associated with a ramp disposed on the support between the dielectric surfaces of the electrodes; the ramp intersecting the first and second contacting surfaces at obtuse and acute angles respectively and providing a surface angularly disposed relative to electric field coupling between the first and second electrode, thereby reducing parasitic effects of the sensed dielectric constant of the liquid.

* * * * *